(12) United States Patent
Bhagavatula et al.

(10) Patent No.: US 9,194,690 B2
(45) Date of Patent: Nov. 24, 2015

(54) POWER TRANSMISSION AND SENSING DEVICE

(71) Applicant: Corning Incorporated, Corning, NY (US)

(72) Inventors: Venkata Adiseshaiah Bhagavatula, Big Flats, NY (US); Theresa Chang, Painted Post, NY (US); Klaus Hartkorn, Painted Post, NY (US); John Himmelreich, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/182,499

(22) Filed: Feb. 18, 2014

(65) Prior Publication Data

US 2014/0247454 A1 Sep. 4, 2014

Related U.S. Application Data

(60) Provisional application No. 61/772,254, filed on Mar. 4, 2013.

(51) Int. Cl.
*G01B 9/02* (2006.01)
*A61B 5/00* (2006.01)
*G02B 6/36* (2006.01)

(52) U.S. Cl.
CPC .......... *G01B 9/02091* (2013.01); *A61B 5/0066* (2013.01); *A61B 5/0084* (2013.01); *A61B 5/687* (2013.01); *A61B 5/6873* (2013.01); *A61B 5/6876* (2013.01); *A61B 2562/12* (2013.01); *A61B 2562/223* (2013.01); *G02B 6/3624* (2013.01)

(58) Field of Classification Search
CPC ...... G01B 9/02; A61B 5/0066; A61B 5/6852; A61B 5/0073; G01N 21/4795
USPC .......................................................... 356/479
See application file for complete search history.

(56) References Cited

U.S. PATENT DOCUMENTS

| | | | |
|---|---|---|---|
| 5,957,941 A | 9/1999 | Ream | |
| 6,445,939 B1 | 9/2002 | Swanson | |
| 6,613,056 B1 * | 9/2003 | Brumbach et al. | 606/128 |
| 2001/0026666 A1 | 10/2001 | Ferrera | |
| 2003/0050663 A1 * | 3/2003 | Khachin et al. | 606/200 |
| 2006/0004404 A1 * | 1/2006 | Khachin et al. | 606/200 |
| 2007/0049911 A1 * | 3/2007 | Brown | 606/12 |
| 2009/0012525 A1 * | 1/2009 | Buehlmann et al. | 606/92 |
| 2009/0247878 A1 | 10/2009 | Tanioka | |
| 2011/0009741 A1 | 1/2011 | Matthews | |
| 2011/0152771 A1 | 6/2011 | Milner et al. | |
| 2011/0164255 A1 | 7/2011 | Konno et al. | |
| 2012/0004506 A1 * | 1/2012 | Tearney et al. | 600/116 |

(Continued)

FOREIGN PATENT DOCUMENTS

WO 2013177154 11/2013

*Primary Examiner* — Tarifur Chowdhury
*Assistant Examiner* — Md Rahman
(74) *Attorney, Agent, or Firm* — Svetlana Z. Short

(57) ABSTRACT

A torque transmission assembly comprising: (i) an optical fiber coupled to an optical sensing component and capable of rotating and translating the optical sensing component and of transmitting light to and from the optical sensing component; and (b) an annular structure surrounding the optical fiber, the annular structure in conjunction with said optical fiber transmits torque from a rotating component to the optical sensing component, wherein the annular structure does not include a steel wire torque spring.

17 Claims, 6 Drawing Sheets

(56) References Cited

U.S. PATENT DOCUMENTS

| | | | |
|---|---|---|---|
| 2012/0071822 A1 * | 3/2012 | Romo et al. ............... 604/95.04 |
| 2013/0038872 A1 | 2/2013 | Fujiwara et al. |
| 2013/0289396 A1 | 10/2013 | Kitatsuji |
| 2013/0331689 A1 | 12/2013 | Le |

* cited by examiner

POWER TRANSMISSION AND SENSING DEVICE

CROSS-REFERENCE TO RELATED APPLICATIONS

This application claims the benefit of priority under 35 U.S.C. §119 of U.S. Provisional Application Ser. No. 61/772,254 filed on Mar. 4, 2013 the contents of which are relied upon and incorporated herein by reference in their entirety.

BACKGROUND

The disclosure relates generally to torque (linear motion and rotation) transmission assemblies and optical sensing devices utilizing torque transmission assemblies, and more particularly to optical coherence tomography (OCT) systems and OCT probe assembles which may be used in medical applications.

Torque transmission and sensing devices, are suitable for use in medical sensing applications, for example, in optical coherence tomography (OCT). In optical coherence tomography, this can be done inside a living body by utilizing a small optical probe component (miniature optic sensor) to image light onto an organic material (for example biological tissue), and to collect the light scattered back by the organic material. The optical probe assembly, including the optical probe component is inserted inside the body, for example through the blood vessels or gastro intestinal tracks, to obtain an image of the inside surfaces of the tissues such as blood vessels, or tissues of the intestinal track.

More specifically the optical probe component moves inside a body to obtain sub-surface 3D (three dimensional) information of tissues. Light back scattered from the tissues at different depths is monitored using the interferometric techniques and a 3D scan of tissues is obtained. The 3D scan is achieved by rotating the optical probe component at high speeds (for example 1000 rpm) in a controlled fashion. This rotation has been achieved using a stainless steel coiled wire torque spring component into which at the fiber and at least a part of the optical probe assembly is incorporated. The stainless steel coiled wire torque spring component and the rest of the optical probe assembly are then threaded through a closely fitting transparent polymer tube referred to as inner lumen. During OCT device operation, the optical probe component and the stainless steel coiled wire torque spring component rotates inside of the inner lumen, and the inner lumen protects the tissues from contact with the rotating probe.

The stainless steel coiled wire torque spring component typically includes multi-coil stainless steel spring, but can include a single wire coil (see FIGS. 1A and 1B, for example). The coiled wire can stretch, so that the spacing between coils can expand or contact under sufficient force. The spring rate k (where k is a spring constant or a force constant of the spring) for such coiled wire torque spring component is around 500N/m under stretching/pulling—i.e., coiled wire torque spring component can stretch relatively easily when pulled. An optical fiber is inserted into the coiled wire torque spring component so that the coiled wire surrounds the fiber. Generally, stainless steel coiled wire torque spring components are comprised of three or more spring coils, with at least two of the spring coils wound in clockwise or counter clockwise direction and at least one other spring coil wound in the opposite direction. Multi-coil stainless steel construction allows these torque spring components to be rotated in either clockwise or anticlockwise direction and transmit the force without unwinding. However, torque spring components with multi-spring coils have the following draw-backs: (1) because of the complexity of these multi-coil springs and their dimensional tolerances, such torque spring components can be quite expensive; (2) because such coiled wire torque spring components are very flexible, threading them through the inner lumen is cumbersome, particularly over a length of a few meters; (3) due to the springs, there can be significant back lash, particularly during the retraction of the probe for scanning, which can lead to image resolution problems and fidelity issues; (4) spiral structure of the spring coils can lead to some stiction while the torque spring component is being threaded inside the inner lumen, which may result in non-uniform rotation and linear motion. A torque spring component made of a single stainless steel coil has similar drawbacks, but may also unwind, or experience greater backlash than the multi-coil torque tube.

No admission is made that any reference cited herein constitutes prior art. Applicant expressly reserves the right to challenge the accuracy and pertinency of any cited documents.

SUMMARY

One embodiment of the disclosure relates to an OCT torque tube comprising:
  (a) an OCT probe component;
  (b) an optical fiber connected to the OCT probe component;
  (c) an annular structure surrounding said optical fiber and capable of translating and rotating the OCT probe.

According to the embodiments described herein the annular structure is a tube not capable of substantial elongation in axial direction. According to some embodiments the tube has an inner wall and an outer wall, the inner wall being continuous.

One embodiment of the disclosure relates to an OCT torque tube assembly comprising:
  (a) an OCT probe component;
  (b) an optical fiber connected to the OCT probe component;
  (c) an annular structure surrounding said optical fiber and capable of translating and rotating the OCT probe component, wherein the annular structure does not include a spring.

One embodiment of the disclosure relates to an OCT torque tube assembly comprising:
  (d) an OCT probe component;
  (e) an optical fiber connected to the OCT probe component;
  (f) an annular structure surrounding said optical fiber and capable of translating and rotating the OCT probe component, wherein the annular structure does not include the multicomponent spring elements wound in opposite directions.

One embodiment of the disclosure relates to an OCT torque tube assembly comprising:
  (a) an OCT probe;
  (b) an optical fiber connected to the OCT probe component;
  (c) a tubular housing with a window structured for the light to transmit from and to the OCT probe component at an angle 70 to 90° relative the optic axis of the OCT probe; and
  (d) an annular structure surrounding said optical fiber and capable of translating and rotating the OCT probe, wherein the annular structure does not include the multicomponent spring elements wound in opposite directions.

Preferably, the annular structure: (a) is flexible so as to be bent to a bend radius r, where 2 cm<r; and (b) has elongation that is less than 5% (e.g., less than 2%, less than 1%) when subjected to axial forces (e.g., force of 10N). Preferably the annular structure has a spring rate k (also referred to as a spring constant or a force constant) of at least 2500N/m (under stretching or pulling), i.e., it is not easily stretchable. Preferably, the annular structure is a tube. According to some embodiments the annular structure comprises at least one of the following:
  (i) multilayers of polymers,
  (ii) multilayers of polymers with at least one of the polymer layers further including reinforcement elements;
  (iii) multilayers of polymers surrounding said fibers, said layers including at least one layer with rigidity <100 MPa and at least one layer with rigidity >400 MPa;
  (iv) a tubular body with multiple perforations around the circumference and along the length of the tubular body.

According to some embodiments, a torque tube comprises: an annular structure coated with material with coefficient of friction being less than 0.3, and preferably less than 0.2. According to some embodiments a torque transmission assembly comprises an annular structure coated with material with coefficient of friction being less than 0.3 an OCT probe housing coated with material with coefficient of friction being less than 0.3 (standard testing according to ATSM standard).

One embodiment of the disclosure relates to a torque transmission assembly comprising: (i) an optical fiber coupled to an optical sensing component and capable of rotating and translating the optical sensing component and of transmitting light to and from the optical sensing component; and (ii) an annular structure surrounding the optical fiber, the annular structure in conjunction with said optical fiber transmits torque from a rotating component to the optical sensing component, wherein the annular structure does not include a steel wire torque spring (e.g., example, the annular structure does not include the multicomponent spring elements wound in opposite directions).

According to some embodiments the annular structure surrounding the fiber is structured to be bendable to a radius r, wherein 1 cm<r and has elongation ΔL under tensile forces of less than 5%. Preferably, according to at least some embodiments, the annular structure is flexible such that 2 cm<r<50 cm, and ΔL≤5%; more preferably 2 cm<r<15 cm and ΔL≤2%, and in some embodiments ΔL≤1%. According to the some embodiments the annular structure is strong enough to withstand tensile forces of greater than 10 Newtons and preferably greater than 50 Newtons (it needs to be strong enough to handle the torque) and has an outer diameter not greater than 2 mm, and preferably not greater than 1.5 mm, for example less than 1.3 mm. According to some embodiments, the annular structure has an outer most layer including material with coefficient of friction being less than 0.3, and preferably less than 0.2.

According to some embodiments the annular structure comprises multilayers of polymers, for example, silicone, acrylates, and/or polyimide. According to some embodiments the annular structure comprises multilayers of polymers, with at least one of the polymer layers being a composite layer that includes at least one polymer and reinforcement elements embedded into the polymer. The reinforcement elements may be, for example, braided or interleaved metal wire, polymer mesh, or reinforcement fibers, and/or carbon filaments. According to some embodiments, the annular structure comprises multilayers of polymer(s) surrounding the optical fiber, wherein the layers include at least one layer with rigidity of less than 100 MPa preferably less than 10 MPa; and at least one layer with rigidity greater than 400 MPA, preferably greater than 500 MPa. According to some embodiments, the annular structure has an outer most layer including material with coefficient of friction of less than 0.3, and preferably less than 0.2.

An additional embodiment of the disclosure relates to an OCT probe assembly comprising: an OCT probe component having an optic axis; an optical fiber having a fiber core, the optical fiber being connected to the OCT probe component such that the optical axis and the core of the optical fiber are preferably coaxial with respect to one another; a tubular housing with a window for light to transmit from and to the OCT probe component at an angle 70° to 90° relative to the optic axis of the OCT probe component (e.g., relative to the optical axis of the fiber core), wherein the annular structure does not include either a single steel torque wire, or multiple torque wires wound in opposite directions. According to some embodiments the annular structure translates and rotates the OCT probe component and comprises at least one of the following: (i) multi-layers of polymers (including silicone, crylates (thermal or uv curable), and/or polyimide); or (ii) multilayers of polymers with at least one of the polymer layers further including reinforcement elements (e.g., interleaved or braided metal wire, carbon filaments, thin metal tube, thin metal tube with perforations, or a polymer mesh, or reinforcement fibers embedded into the polymer and surrounding the optical transmission fiber; or (iii) multilayers of polymers surrounding the optical fiber, these layers including at least one layer with rigidity less than 100 MPa (preferably less than 10 MPa) and at least one layer with rigidity greater 400 MPA (preferably greater than 500 MPa). According to some embodiments the annular structure has a coating or an outer surface with a coefficient of friction that is less than 0.3, and preferably less than 0.2.

Preferably, the annular structure and the optical fiber form a unitary, integral component. For example, according to at least some embodiments the optical fiber is permanently bonded to the annular structure along the length of the fiber. Preferably, the annular structure that translates and rotates the OCT probe component is a multi-layer fiber coating. According to some embodiments the optical fiber in conjunction with the annular structure forms a jacketed or coated fiber, forming a single, integral component. According to some embodiments this coating or jacket has an outer most layer having at least one material with coefficient of friction that is <0.3, and preferably <0.2.

Additional features and advantages will be set forth in the detailed description which follows, and in part will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

FIGS. 1A and 1B are schematic depictions of prior art stainless steel coiled wire torque spring components made of wire coils WC surrounding an optical fiber OF.

DETAILED DESCRIPTION

Some embodiments of the disclosure relate to a torque transmission assembly 5 that include: (i) an optical fiber 20 coupled to an optical sensing component 10 and capable of transmitting light to and from the optical sensing component; and (ii) an annular structure 30 having a continuous cross-section, the annular structure 30 surrounding the optical fiber 20 and being configured such that the annular structure 30 in conjunction with the optical fiber (a) transmits torque from a rotating component to the optical sensing component 10, (b) rotates and translates the optical sensing component 10, wherein the annular structure 30 does not include a steel wire torque spring (e.g., example, the annular structure does not include multicomponent spring elements wound in opposite directions). Preferably, according to the embodiments described herein, the annular structure is a tube surrounding the optical fiber and has elongation $\Delta L$ under tensile forces of less than 5%, for example $\Delta L \leq 2\%$ or $\Delta L \leq 1\%$.

According to some embodiments, the torque transmission assembly 5 is an OCT probe assembly 5' and the optical sensing component is the OCT probe component.

Figure 1A:
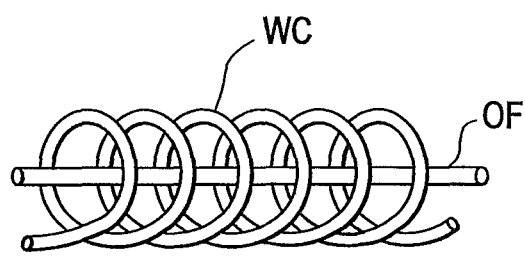
Figure 1B:
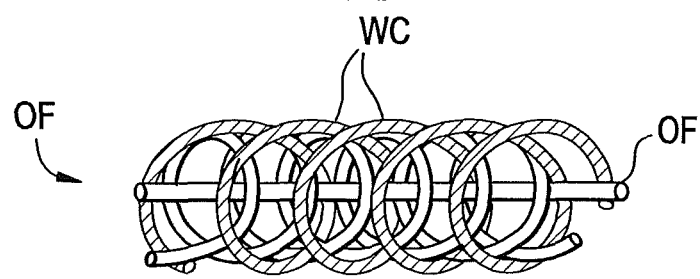
Figure 2:
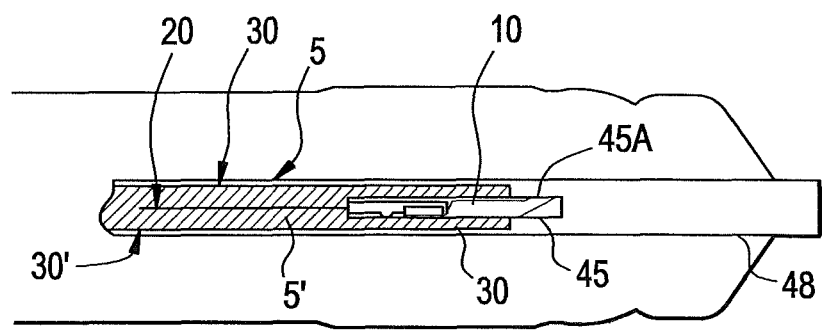
FIG. 2 is schematic of an embodiment of the OCT probe assembly.

As shown schematically in FIG. 2, according to some embodiments, the OCT probe assembly 5' includes: (i) an OCT optical probe component 10 (also referred herein as a micro-optic element, optical sensing element, or a miniature optic sensor) having an optic axis OA; an optical fiber 20 having a fiber core 20' (not shown), the optical fiber being functionally connected to the OCT optical probe component such that the optical axis OA and the core 20' of the optical fiber 20 are coaxial with respect to one another; (ii) a tubular housing 45 with a window 45A for the fight to transmit from and to the OCT optical probe component 10 at an angle 70° to 90° relative the optic axis of the OCT probe component (i.e., relative to the optical fiber core); and (iii) an annular structure 30 surrounding the optical fiber 20, wherein the annular structure 30 does not include either a single steel torque spring wire, or multiple torque spring wires wound in opposite directions. The annular structure has a tubular body. Preferably, according to some embodiments, the annular structure 30 and the optical fiber 20 form a unitary, integral component. In the embodiments described herein the annular structure 30 is a tube not capable of substantial elongation in axial direction.

According to some embodiments the tube has an inner wall and an outer wall, the inner wall being continuous.

The following embodiments of the invention can be utilized in optical coherence tomography (OCT). An OCT system 2 (not shown), according to one or more embodiments described herein, allows one to obtain sub-surface 3D information by collecting light signal back scattered from the tissues at different depth, and monitoring or analyzing the collected signal light by using interferometric techniques, to obtain a 3D scan of the scanned tissue. The 3D scan is achieved by rotating the OCT optical probe component 10 at high speed, for example at around 1000 rpm or more in a controlled fashion. For example, for some cardiac applications the rotation speed of the optical probe component 10 may be 3000-12000 rpm. This rotation is achieved using an optical fiber 20 (which transmits light to and from the optical probe component) and the annular structure 30. As stated above, the annular structure 30 does not include a steel wire torque spring, nor does it includes the multicomponent steel spring elements wound in opposite directions. It has a tubular body and is not helical. The annular structure 30 surrounding the optical fiber 20, in conjunction with the optical fiber 20, transmits torque from a rotating component 40' (not shown) to the optical probe component 10 (i.e., the optical sensing component). More specifically, the annular structure 30 surrounds the optical fiber 20 and is functionally coupled or is physically attached to the OCT optical probe component 10 and/or its tubular housing 45, and serves the function of transmitting the linear motion from an actuator 40 (not shown) and rotary motion from the a rotary motion actuator and/or rotating component such as the rotary joint 40', situated outside the body to the OCT optical probe component 10 to obtain the 3D scan of the test sample (e.g., of the biological tissue). According to at least some embodiments, a tubular housing 45 surrounds at least a portion of the OCT optical probe component 10. The tubular housing 45 has a window 45A to transmit light from the OCT probe component 20 to the tissues under observation and to allow scattered light to be transmitted back to the OCT probe component 20, preferably at an angle 70° to 90° relative the optic axis of the OCT optical probe component. The window 45A may be an optically transparent glass or plastic, or just a perforation in the tubular housing 45. The optical probe component 10, the optical fiber 20, the annular structure 30 surrounding this optical fiber 20, and the tubular housing 45 surrounding at least a portion of the OCT probe component 10, form an OCT probe subassembly 5' that is threaded through a closely fitting transparent polymer tube referred to as the inner lumen 48. A schematic of one embodiment of such an OCT probe assembly 5' is illustrated in FIG. 2.

According to some embodiments the annular structure 30 translates and rotates the OCT optical probe component 10 and further comprises at least one of the following: (i) multilayers of polymers (including silicone, acrylates (thermal or uv curable), and/or polyimide); or (ii) multilayers of polymers with at least one of the polymer layers further including reinforcement elements R (e.g., interleaved or braided metal wire, thin metal tube, thin metal tube with perforations, or a polymer mesh, reinforcement fibers and/or carbon filaments embedded into the polymer and surrounding the optical fiber; or (iii) multilayers of polymers surrounding the optical fiber, these layers including at least one layer with rigidity less than 100 MPa (preferably less than 10 MPa) and at least one layer with rigidity greater than 400 MPA (preferably greater than 500 MPa). According to other embodiments the annular structure 30 is a plastic or metal tube with multiple holes or perforations therein. These holes or perforations are created, for example, by laser cutting and/or drilling. According to yet other embodiments the annular structure 10 is a polymer jacket (e.g., an extruded polymer jacket) surrounding the optical fiber 20. The jacket and the optical fiber 20 form a single integral component (i.e., they are fused or otherwise bonded to one another).

For example, according to at least some of these embodiments, the optical fiber 20 is permanently bonded to the annular structure 30 along the length of the fiber. Preferably, the annular structure 30 that translates and rotates the OCT probe component is a multi-layer fiber coating. According to some embodiments this coating has an outermost layer having at least one material with coefficient of friction that is less than 0.3, and preferably less than 0.2.

The annular structure 30 is flexible and, according to the exemplary embodiments disclosed herein, is able to transmit torque for both clockwise (CW) and counter clockwise (CCW) rotations, while faithfully transmitting the actuator motion to the optical probe component 10 without backlash. Otherwise, the reproduction of the images will have errors associated with this backlash. The exemplary embodiments of the annular structures 30 are flexible, in order to allow its passage through narrow channels like blood vessels, esophagus, or intestinal tracts. For esophageal OCT applications, the bend radius r is in the range of about 5"-6" (i.e., $12.5 \leq r \leq 15.5$ cm), whereas for cardiac and other applications involving small blood vessels, the bend radius r is preferably about 1"-2" (i.e., $2.5 \text{ cm} \leq r \leq 5.1 \text{ cm}$).

According to some embodiments the annular structure 30 is structured to be bendable to a radius r, wherein 2 cm<r, and has elongation $\Delta L$ under tensile forces of less than 10%, and preferably less than 5%. Preferably, in some embodiments 2 cm<r<50 cm and $\Delta L \leq 5\%$, more preferably $\Delta L \leq 2\%$ and even more preferably $\Delta L \leq 1\%$. According to the disclosed embodiments the annular structure 30 is strong enough to withstand the forces and torques involved in high speed rotation and strong axial forces (pulling), e.g., tensile forces of greater 10 Newtons and preferably greater than 50 Newtons. For example, the pull forces experienced in esophegial OCT applications are in the range of about 10 Newtons. The annular structure 30 has a spring rate k (also referred to as a spring constant or a force constant herein) of at least 2500N/m (under stretching or pulling), more preferably of at least 3000N/m, i.e., the annular structure 30 is not easily stretchable. For the embodiments of the OCT probe assembly, the adhesion of the annular structure 30 to the OCT optical probe component 10 and/or the tubular housing 45 is greater than 10 Newtons. The annular structure 30 has an outer diameter d that is not greater than 3 mm, and preferably not greater than 2 mm, even more preferably d<1.5 mm (e.g., d<1.3 mm, or d<1.2 mm, and in the embodiments described herein d≤1 mm).

According to the exemplary embodiments described herein the outer diameter d of the annular structure 30 has does not vary more than about 100 μm over the length of the annular structure 30. The inner diameter of the annular structure 30 is greater than that of the optical fiber 20 in order to accommodate the optical fiber 20 situated therein. Preferably the inner diameter of the annular structure 30 is greater than 100 μm and more preferably greater than 125 μm.

For example, in some embodiments the outer diameter d of annular structure 30 is of 0.8 mm≤d≤1 mm, the inner diameter of the annular structure 30 is about 400 μm to 600 μm, and the outer diameter of the coated fiber is 200 μm-300 μm. In one embodiment d=950 μm, the outer diameter of the coated fiber 20 is 250 μm and the inner diameter of the annular structure 30 is about 500 μm. That is, in this embodiment the inner diameter of the annular structure 30 is 250 μm greater than the outer diameter of the coated optical fiber 20 inserted therein.

The OCT probe assembly with the annular structure 30 described herein can advantageously meet at least one of the following requirements are: (1) low friction, (2) strength to transmit the torque force to the OCT optical probe component 10, and/or to the tubular housing 45 that at least partially surrounds the OCT optical probe component 10, (3) flexibility to thread through small radii bends without kinks, (4) fidelity and low backlash in transmitting the motion of the rotational and linear motion actuators to the optical probe tip or to the OCT optical probe component 10, for good image resolution and fidelity.

The annular structure 30 is preferably kink resistant to prevent the optical probe component 10 (i.e., the optical sensing component) and the optical fiber 20 from experiencing high losses or breakage. Thus, preferably, the outer surface 30' of annular structure 30 has a low frictional coefficient (for example <0.3 and in some embodiments ≤0.2) to facilitate easy threading of the torque transmission assembly 5 (e.g., the OCT probe assembly) through the inner lumen 48 and to minimize or to prevent stiction. Preferably, at least one surface (e.g., the front end or the outer surface 45') of tubular housing 45 also has a low frictional coefficient (for example <0.3 and in some embodiments ≤0.2) to facilitate easy threading of the torque transmission assembly 5 (e.g., the OCT probe assembly 5') through the inner lumen 48, and to minimize or to prevent stiction and/or tearing of the inner lumen. According to some embodiments, the annular structure 30 is kink resistant due to low friction material on or in its outermost layer, wherein this material with coefficient of friction <0.3, and preferably <0.2. Finally, the annular structure 30 is made of materials that withstand the environmental conditions and requirements of the specific application. For example, the embodiments of the OCT probe assembly 5 are structured to withstand the storage temperatures, humidity conditions, and assembly conditions required. For example, they can withstand temperatures as high as 100° C. and storage temperatures as low as 0° C. These embodiments advantageously provide low backlash in transmitting the motion of the rotational and linear motion actuators to the optical probe tip for good image resolution and fidelity. This requirement is met by OCT probe assembly that can rotate uniformly as it is rotating and being pulled back to scan the organ. Advantageously in the exemplary embodiments described herein the uniformity of rotation is not less than 10%, for example within preferably 5%, for example ≤2%, or ≤1%.

Various embodiments will be further clarified by the following examples.

EXAMPLE 1

Torque Transmission Tubes. With reference to FIGS. 3A, 3B and 4-6C, some exemplary embodiments of torque transmission components (i.e., annular structure 30) are reinforced co-extruded coatings, or reinforced tubes that surround the optical fiber 20. The coatings or tubes 30A of the annular structure 30 may be reinforced, for example, by the reinforcement elements R such as thin metal wire meshes, wire spirals, polymer mesh(es), reinforcement fibers, or carbon filaments. That is, reinforcement components R are imbedded in the tubular body of annular structure 30. The torque transmission tubes 30A that form the annular structure 30 have an inner diameter that is slightly larger than the outer diameter of the optical fiber 20.

Figure 3A:
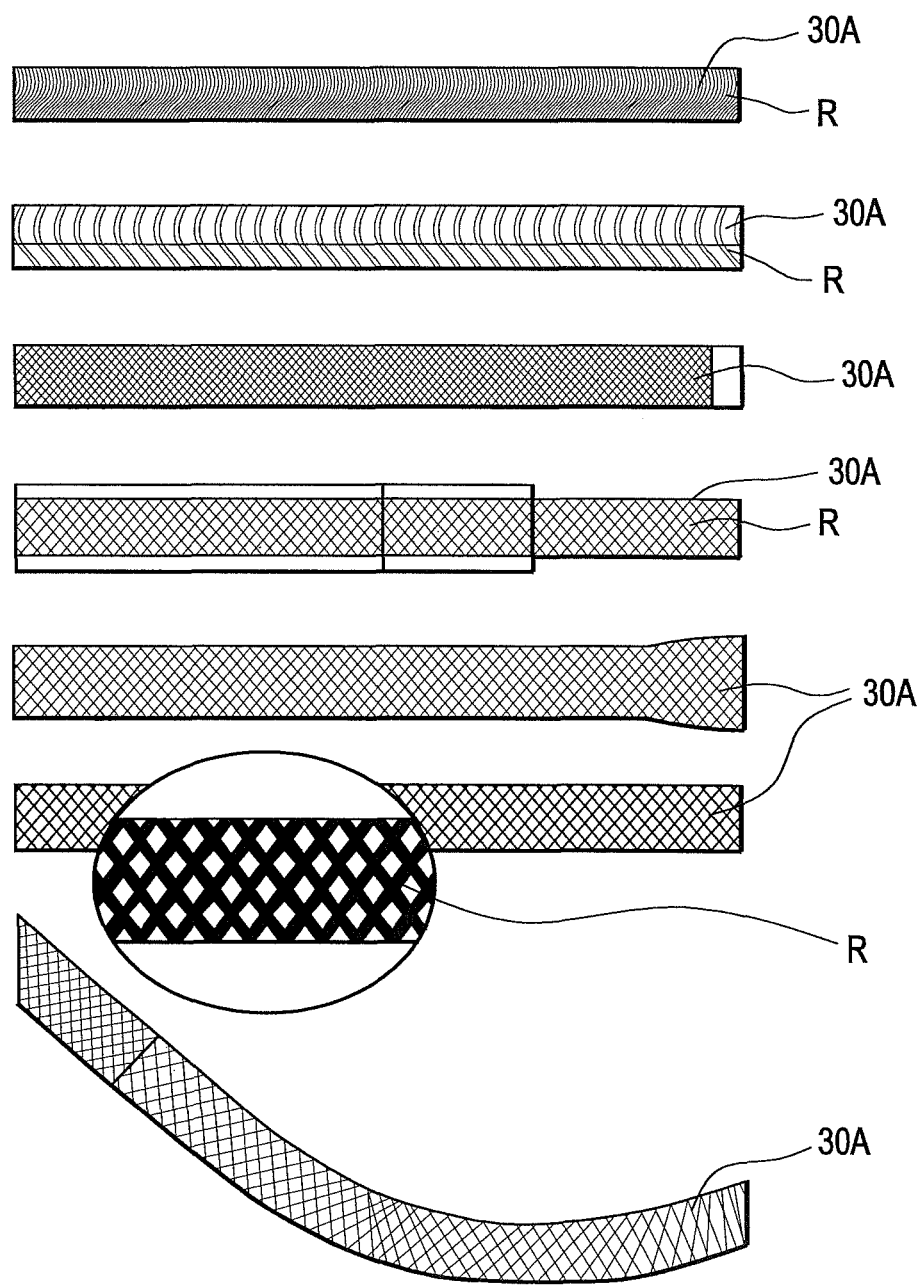
FIG. 3A illustrate torque transmission components that comprise an annular structure made of extruded polymers with embedded reinforcement meshes.

FIG. 3A illustrates several medical grade polymer tube structures 30A (also referred to herein as torque transmission tubes) that can be used as the annular structure 30 for torque transmission applications. The torque transmission tubes 30A are extruded polymers with embedded reinforcement meshes as shown in FIG. 3A. The torque transmission polymer based tube 30A has an inner diameter large enough so that the optical fiber 20 can be threaded through the tube tubes 30A. The torque transmission tube 30A surrounds the optical fiber 20 and is functionally coupled or is physically attached to the OCT optical probe component 10 and/or its tubular housing 45, and serves the function of transmitting the linear motion from an actuator 40 and rotary motion from the a rotary motion actuator and/or rotating component (rotary joint 40', not shown) situated outside the body to the OCT optical probe component 10 to obtain the 3D scan of the test sample (e.g., of the biological tissue). For example, in some embodiments the outer diameter d of the torque transmission tubes 30A are 0.8 mm≤d≤1 mm, the inner diameter is about 400 µm to 600 µm, and the outer diameter of the coated fiber 20 inserted inside the torque transmission tubes 30A is about 200 µm-300 µm.

The torque transmission tubes 30A can be made with different materials that satisfy the strength, frictional coefficient and other requirements. The reinforcement mesh can be made of metal or polymer fibers of different sizes and woven into different mesh structures to balance flexibility with strength and kink resistance. The tubes 30A can be extruded with very good dimensional tolerances of better than 50 µm. FIG. 3A illustrates an expanded view of the reinforced braided tube (annular structure 30, (see the second from the bottom) that shows the details of a polymer material and the reinforcing wire mesh structure. The wire mesh is woven and interweaved. The thickness of the reinforcing wire is 50 µm-100 µm and the wire can be steel. It can be round or flat. The polymer material that surrounds the wire and forms the tubular body of this type of the annular structure 30 can be Polyimide, PTFE, Nylon, or urethane(s). These types of annular structure 30 can be made by different commercial vendors. Similar tubes can obtained, for example, from Microlumen Inc, located at One Microlumen Way, Oldsmar, Fla. 34677, and according to some embodiments can be placed around the optical fiber 20, coupled to the motion actuator 40 and the rotary joint 40' on one end and to the optical sensing component 10 on the other end, and utilized as annular structure 30 for torque transmission. The construction of the reinforced braided tube annular structure 30 includes a substrate layer, braided or coiled layer and an exterior layer. The substrates layer can include polyimide, PTFE composites or pure PTFE liners. Pure PTFE liners and PTFE composites offer reduced surface friction. The exterior layer is typically constructed of Polyimide, but can be comprised of thermoplastics like Pebax, Nylon & Urethanes. It is noted that the annular structure 30 is reinforced wire mesh structure. The wires or filaments situated within the annular structure 30 serve as structural re-enforcement and not as a spring, i.e., they are not structured or situated to act as a mechanical spring element.

EXAMPLE 2

Perforated tubes. Another embodiments of torque transmission components (i.e., annular structure 30) are polymer or metal tubes 30B, 30B' with multiple holes 11, slots or other perforations around the circumference and along the length of the tubular body to create "open areas". The torque transmission tubes 30B, 30B' can be, for example, laser processed by cutting arrays of holes and/or spiral slots in the tubular body. (See, for example, FIG. 3B.) That is, the annular structure 30 may be a laser processed tube 30B, 30B' where the tube is made, for example, of plastic or metal. The tubes 30B can be coated with low friction coatings 60 and preferably have coefficient of friction that is less than 0.3, and more preferably not greater than 0.2. The details of the low friction coating are given in the following sections. The torque transmission tubes 30B serve the function of transmitting the translational and rotary motions from the actuator 40 and the rotary joint 40' situated outside the body to the optical sensing component such as the OCT optical probe component 10 to obtain the 3D scan of the test sample.

Polymer based tubes 30B can made of materials suitable for the OCT application and can be extruded with good dimensional control. To provide the flexibility and other functionalities, holes and slots etc., are incorporated into tubes 30B. Lasers can be used to generate these controlled patterns and these processes are amenable to mass production. The range of open areas (for example areas removed by laser process) to remaining material range from 0.2 to 0.8. Preferably, in order to provide enough torsional stiffness without compromising the flexibility, the preferred ratio is closer to 0.5 (for example 0.4-0.6). Lasers can also be utilized to create holes, slots or perforations in metal tubes 30B'.

Figure 3B:
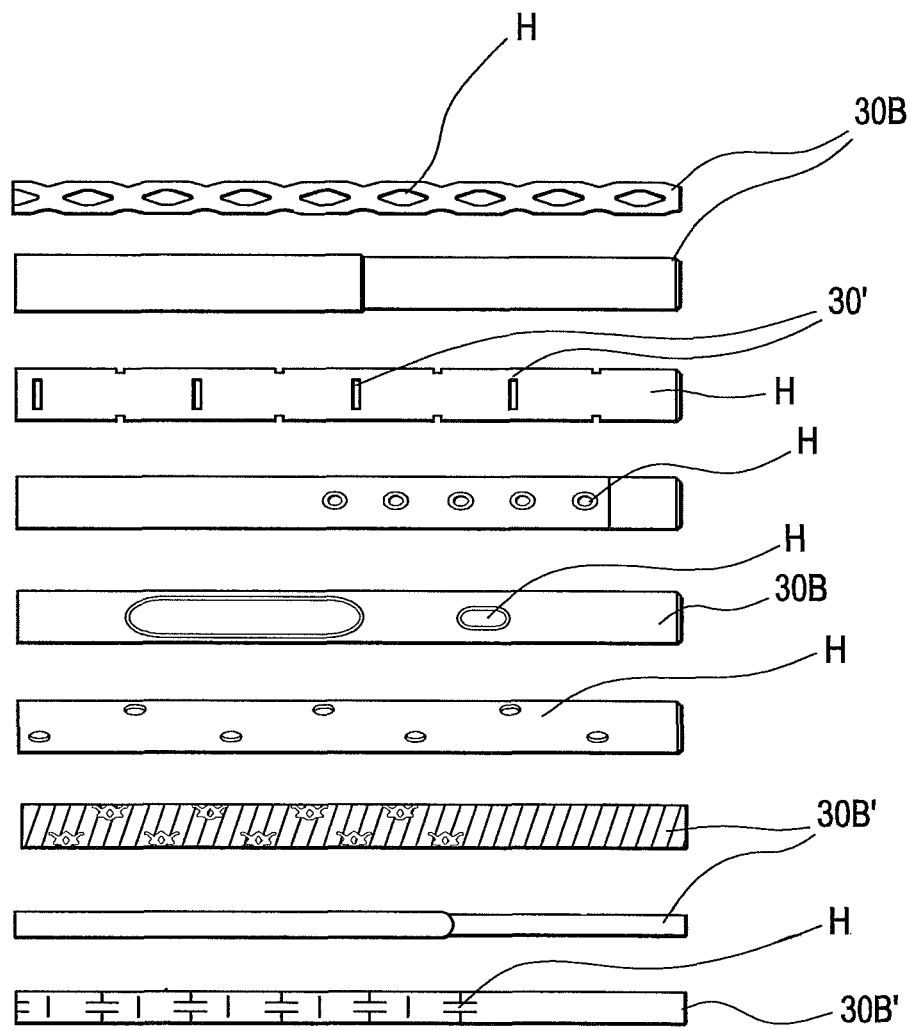
FIG. 3B illustrate torque transmission components that comprise an annular structure with holes, perforations and/or slots.

More specifically, FIG. 3B illustrates polymer tube structures where the annular structures 30 are made of solid tubes 3013 that are laser machined to have arrays of holes and slots etc., and provide the flexibility and low frictional forces. FIG. 3B also illustrates metal tube structures where the annular structures 30 are made of solid tubes 30B' that are laser machined to have arrays of holes H, slots etc., and provide the flexibility and low frictional forces.

EXAMPLE 3

Figure 4A:
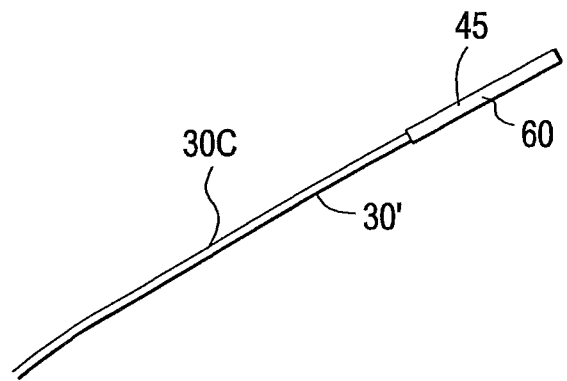
FIGS. 4A and 4B illustrate two other embodiments of the torque transmission component.
Figure 4B:
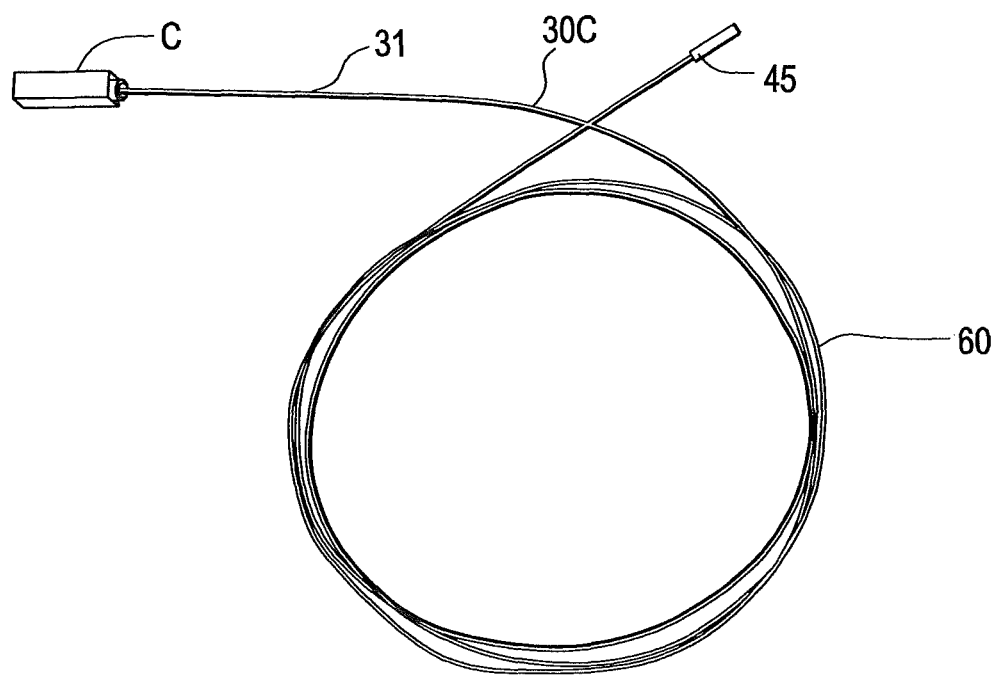
Figure 5:
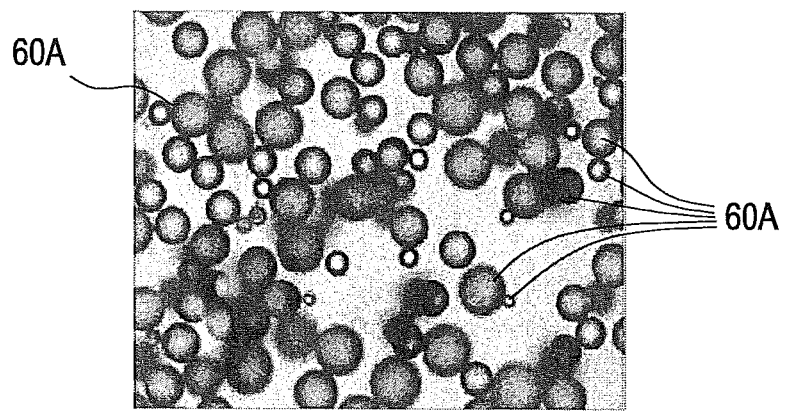
FIG. 5 illustrates one or more embodiments of low friction beads.

Integrated jacketed fiber. According to some exemplary embodiments, the OCT probe assembly 5' contains a low cost annular structure 30, for example a unitary structure such as an integrated jacketed fiber 30C (also referred to herein as a jacketed fiber torque tube). The integrated jacketed fiber 30 integrates a suitable optical fiber 20 (e.g., a single mode fiber) with a suitable jacket 30' in a single component 30C. This annular structure 30 (via the integrated jacket 30') can serve to transmit the torque needed to rotate the optical probe component 10 at high speed. Thus, annular structure 30 serves the function of transmitting the rotary motion from the motion actuator 40 and the rotary joint 40' situated outside the body to the optical sensing component such as the OCT optical probe component 10 while providing light to and from the optical probe component 10, to obtain the 3D scan of the test sample. The integrated jacketed fiber embodiment of the annular structures 30 disclosed herein provides the same functionality as the prior art stainless wire coiled torque tubes, but overcomes at least some of their limitations. For example, the integrated jacketed fiber embodiments disclosed here combine the optical fiber 20 (e.g., a single mode fiber) and integrated jacket 30' into a single integrated unit 30C and eliminate the need for a separate stainless wire coiled torque tube and the associated cost and assembly steps, while reducing or eliminating backlash and/or providing improved rotation uniformity. In this embodiment, the single mode fiber or other suitable optical fiber 20 used in OCT probe assembly can be extruded or drawn with a jacket material of appropriate dimensions. For example, for esophageal OCT applications, the optical fiber 20 can be extruded with a jacket 30' that is 900 µm-950 µm in diameter, as shown in FIG. 4A. That is, the jacket 30' surrounds the optical fiber 20 and is permanently attached to the fiber, i.e., it forms a jacketed fiber torque tube 30C. The integrated jacket 30' can be made of appropriate material for example Nylon, Silicone, Hytrel etc., to meet the requirements of this application. For example, the jacket materials are selected to protect the optical fiber 20 and to also advantageously meet the flexibility, strength, and other mechanical and environmental requirements to be met by the OCT probe. Examples of these requirements are: 1) low friction, 2) strength to transmit the torque force (or rotational stiffness), 3) flexibility to thread through small radii bends without kinks, 4) low backlash in transmitting the motion of the rotational and linear motion actuators to the tip optical probe component, for good image resolution and fidelity. Some of the embodiments include composite reinforcement structure R such as, for example, metal meshes and/or polymer wires and meshes for additional kink resistance and to provide structural "reinforcement" to the integrated jacketed fiber and tubes, so that it has the required strength to transmit the high speed rotational motion from a rotational motion actuator to the optical probe component.

The jacket 30' of the integrated jacketed fiber torque tube 30C of FIG. 4A has no additional reinforcement structures incorporated therein. The coating (jacket) material is flexible and can be chosen to meet the desired flexibility, strength and frictional coefficient characteristics. Examples of material options for the integrated jacketed fiber torque tube 30C are PVC, Hytrel, nylon, and LCPC (Liquid Crystal Polymer coatings). The processes used for putting these integrated jackets 30' on SM (single mode) optical fibers may be, for example, either an extrusion process or a fiber draw coating process. The integrated jacketed fiber torque tube 30C of FIG. 4A is attached to the housing 45 of the OCT probe assembly 5'. The other end of the integrated jacketed fiber torque tube 30C is attached, for example, to a steel tube guide 31 that may surround the integrated jacketed fiber torque tube 30C. This is illustrated, for example, in FIG. 4B. The steel guide tube 31 and the jacketed optical fiber 20 are connected to a fiber connector C (FIG. 4B) that can couple to on an optical rotary joint (rotating component 40', not shown). The rotary joint 40' (not shown) couples the light from the source to the optical fiber 20. The rotary joint 40' allows the OCT torque tube assembly also to rotate freely. In the embodiment depicted in FIG. 4, the length integrated jacketed fiber torque tube 30C is about 2.5 meters.

For additional strength, the integrated jacketed fiber torque tube 30C can be embedded with reinforcements, similar to those shown in FIG. 3A. In this embodiment, the jacket 30' includes metal or polymer reinforcements that are coextruded or drawn along with the single mode fiber of this embodiment. The polymer or metal reinforcement wires can be made, for example, of nylon and steel, and can have diameters in the range from about 50 µm to about 100 µm. The jacket material can be, for example, any of the extrusion compatible polymers such as PVC, Hytrel, Nylon, or silicone. The jacket material utilized in a fiber drawing process can be, for example, a UV curable material such as a UV acrylate or silicone, or other thermally curable material. It can be made of a single coating or multiple coatings. The outer coating can comprise of a thin low friction material like Teflon, etc. Integrated jacketed fiber embodiments have several advantages. The integrated jacketed fiber embodiment disclosed here combines the optical fiber and the torque tube into a single integrated unit and eliminates the need for a separate torque tube and the associated cost and assembly steps. The integrated fiber jacket can be made, for example, of appropriate material such as Nylon, silicone, Hytrel etc. The jacket materials are selected to protect the optical fiber (e.g., a single mode fiber) and also meet the flexibility, strength, and other mechanical and environmental requirements to be met by the OCT probe.

The jacket 30' of the integrated jacketed fiber 30C may have a low friction outer layer and may be coated with a low friction coating 60, in order to make it more slippery. The low friction outer layer can be obtained by applying micron/submicron coatings of Teflon or Fluro-silane polymers on the outer surface of the jacket 30'. The low friction coating 60 can also be obtained by filling the UV coating materials with, for example, 0.5 µm-50 µm diameter beads 60A of low friction materials. Examples of low friction materials and beads are thin Teflon coating or beads, or TexMatte 6025 (PMMA) 25-30 µm diameter particles. (See, For example, FIG. 5). Such beads or particles can reduce frictional forces by a factor of 2 to 3, or more. The low friction coatings 60 and/or beads 60A can be produced, for example, in two ways: (1) they can be mixed into the jacket material and can be drawn or extruded as jackets; or (2) the low friction materials and beads can be applied as outer coatings on top of other surfaces. These coatings can be as thin as 0.1-2 µM, or thicker (for example 100 µm). For example, some of the Teflon or fluoro polymer coatings 60 can be applied as an outer coating on the outer surface of the jacket 30' using a dip coating technique or a or spray coating technique, and then cured by heat or by UV light. The low friction beads 60A can also be incorporated into the jacket material, or applied as an additional coating 60 over the standard jacket material.

As shown in FIG. 3B (second tubular component, from the top) the jacket 30' can have thicker or thinner areas (for example areas of material removed by laser processing), in order to improve flexibility while maintaining torsional stiffness. The ratio of thicker to thinner material area can range from 0.2 to 0.8. Preferably, in order to provide enough torsional stiffness without compromising the flexibility this ratio is close to 0.5 (for example 0.4-0.6).

EXAMPLE 4

Fiber coatings. According to some embodiments the annular structure 30 is a coating 30D on the optical fiber 20. The coating 30D comprises multilayers 50$i$ of polymers, for example, silicone, acrylates, and/or polyimides. For example, according to some embodiments, the annular structure 30 comprises multilayers 50$i$ of polymers, with at least one of the polymer layers being a composite layer that includes at least one polymer and reinforcement elements R embedded into the polymer. As described above, the reinforcement elements R may be: braided or interleaved metal wire, polymer mesh, reinforcement fibers, and/or carbon filaments. According to some embodiments, the annular structure 30 of this embodiment has an outermost layer that includes material with coefficient of friction <0.3, for example ≤2. According to some embodiments, the annular structure 30 has an outer a coating layer 60 with coefficient of friction <0.3, and preferably <0.2. According to some embodiments the layers 50$i$ include at least one layer with rigidity of less than 100 MPa and preferably less than 10 MPa; and at least one layer with rigidity greater than 400 MPA, preferably greater than 500 MPa. The coated optical fiber forms a single, unitary component that is able to transmit the torque needed to rotate the optical probe component 10 at high speeds, while providing light to and from the optical probe component 10.

Multi-layer fiber coating utilization for an integrated torque tube, to be used as the annular structure 30 allows the use of a low cost fiber draw process with UV curable coatings and extrusion process with thermal setting and thermoplastic epoxies and polymers. An example of this multi-later integrated torque tube is shown in the FIGS. 6A-6C. The multi-layer structure is built up by coating alternate layers of UV coatings with different rigidity on a standard Single Mode fiber 20. By controlling the layer thicknesses of the high and low rigidity layer materials, a balance between rigidity and flexibility is achieved. These multi layers 50i can be build up with a multi-step draw or an extrusion process. An example of this multi-step draw process can utilize a spool of 250 µm (outer) diameter SMF fiber (comprising a 125 µm single mode glass fiber with a layer each of a primary and a secondary UV curable acrylate coatings) is run through the draw tower to put on additional coatings of low and high rigidity UV curable coatings, and is built up from 250 µm the outer diameter of the coated fiber for example to 600 µm and wound onto a take-up spool. This coating application process is repeated to build up the coatings layers until the desired outside diameter OD of the coated fiber is achieved (e.g., OD=950 µm). This multi-step draw process allows good curing of the UV coatings and a better controlled coating geometry and properties to be obtained.

Figure 6A:
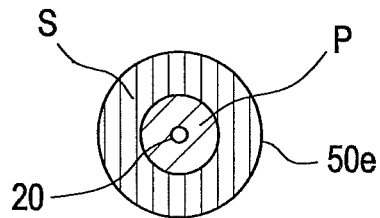
FIGS. 6A-6C illustrates one or more embodiments of the torque transmission component present invention.
Figure 6B:
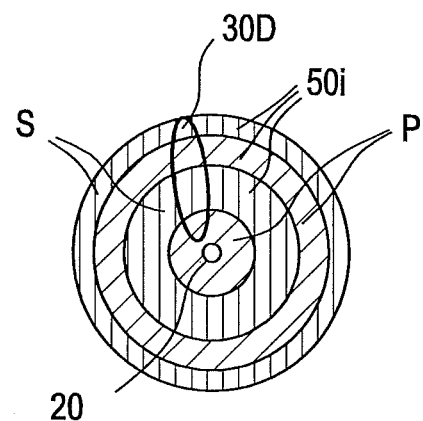
Figure 6C:
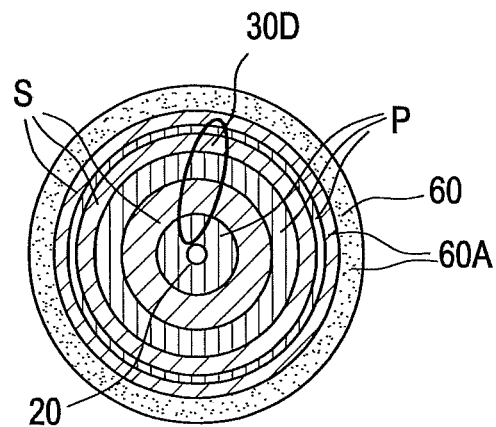

The annular structure 30 of this embodiment may include multiple coating layers 50i made of polymers, wherein the multiple coating layers 50i include at least one layer with rigidity <100 MPa; and at least one layer with rigidity >400 MPa. For example the annular structure 30 may include at least one layer with rigidity <50 MPa (e.g., a primary coating layer P situated adjacent to the fiber having rigidity 0.3-10 MPa; and at least one coating layer S with rigidity >600 MPa (secondary coating layer being situated over the primary coating layer, and having rigidity between 700 and 1200 MPa). The outermost layer may have coefficient of friction less than 0.3, and may be the coating 60 described herein, as shown in FIGS. 6A-6C. The low friction outer layer can be obtained, for example, by coating micron/sub-micron coatings of Teflon or Fluro-silane polymers over the multiple coating layers 50i described above. A low friction coating 60 can also be obtained by filling the UV coating materials with micron sized beads of low index materials, for example, 0.5 µm-50 µm diameter beads of low friction materials. For example, beads of low friction materials may be Teflon or TexMatte 6025 (PMMA) 25-30 µm diameter particles. In some embodiments the bead diameters are ≤10 µm (e.g., 1-8 µm), in some embodiments ≤5 µm (1-5 µm). Such beads or particles can reduce frictional forces by a factor of 2 to 3, or more. The low friction coatings 60 and beads can be produced, for example, in two ways: (1) They can be mixed into the jacket material and can be drawn or extruded as jackets; or (2) the low friction materials and beads can be applied as outer coatings on top of other surfaces. The low friction coating 60 can be as thin as 0.1-2 µm, or thicker. For example, some of the Teflon or fluoro polymer coatings can be applied as an outer coating over the fiber's multi-layer coating using a dip coating or a spray coating technique, and then heat or UV cured. The low friction beads can also be incorporated into these materials or the applied as an additional coating over the fiber's multi-layer coating 30D.

Several reels (1, 2, and 10 km (kilometers)) of such integrated torque tube SMF-28 fibers with multi-layer design and about 950 µm OD have been drawn using the multi-step draw process. Lower friction outer coatings also have been applied on the resulting torque tubes.

Exemplary materials and/or the material properties for the multilayer coatings 50i are provided below. Some of these materials were developed for optical fibers designed for telecommunication applications. Applicants discovered that similar materials can be used for the for the multilayer coatings 50i for the OCT integrated torque tube applications. In OCT torque tube applications, the micro-bending requirements and environmental requirements are not as stringent as in telecommunication applications, because only a few meters of optical fiber is used the OCT applications, as opposed to 10's-100's of kms of fiber for telecomm applications. Thus, fiber's micro-bend loss is not as critical in OCT applications. Therefore, applicants discovered that in OCT applications, coatings 50i made of UV curable acrylates, and silicones can also be utilized.

Losses, due to micro-bending, could be reduced by shielding the optical fiber 20 from outside forces by using a soft inner coating layer, having a modulus of 14,000 psi (~100 MPa), and an outer shell (also referred to herein as the outer coating layer) made of a material having a modulus of 140,000 psi (about 1000 MPa). The inner coating layer is designed to act as a shock absorber, and is situated under the tougher outer coating layer, to minimize attenuation due to microbending. In this embodiment, the inner coating layer has a very low crosslink density and a modulus of 0.5 MPa-3 MPa. The inner coating layer is preferably structured to adhere to the glass (when the cladding layer of the optical fiber 20 is glass), yet strip cleanly from the glass, to facilitate splicing and connecting.

The outer coating layer (which surrounds at least the primary coating layer) sometimes called the secondary coating, protects the inner coating layer (also referred to herein as a primary coating layer P) against mechanical damage and acts as a barrier to lateral forces. It also serves as a barrier to moisture. The outer coating layer is a hard coating, having a high modulus and high Tg (glass transition temperature), to facilitate good handling and durability. It is generally fast curing for ease of processing, and has good chemical resistance to solvents, cable filling gels and moisture. The surface properties of the secondary coating layer S can be carefully controlled, to allow good adhesion of the ink, used in color identification, while at the same time allowing for good winding onto take-up spools. The secondary coating layer(s) S have higher rigidity than the softer primary coating layer(s) P.

Low friction coatings. Some embodiments of torque transmission components (i.e., annular structure 30) utilize low friction coatings 60 on OCT probe components such as tubular housing 45 and/or the annular structures 30. One of the requirements for the torque transmission components (i.e., annular structure 30) is low friction between the annular structure 30 and the inner lumen tube 48. The clearances between the torque tube and the inner lumen need to be kept as small as possible to enable the annular structure 30 to have controlled rotation at high speed. It is noted that if low friction coatings or materials are not utilized, with small clearances the frictional forces can be significant, particularly while threading the annular structure 30 through small radius bends. This increase in torque force can lead to failures in the OCT probe assembly. To minimize such effects, it is advantageous to reduce the frictional forces.

Low friction coatings 60 on the surface of the annular structure 30 can be created via:

1) application of low friction coating material coatings during the fiber coating draw, as the last coating layer;

2) extrusion process (for example to create a low friction jacket around the fiber);

3) spray coating of low friction coating material(s) on another coating, or on the outer surface of the annular structure 30; or 4) dip coating of low friction coating material(s) onto another coating, or onto the outer surface of the annular structure 30.

In some embodiments the thicknesses of low friction coating(s) 60 on the surfaces of the annular structure 30 are 5 μm to about 1500 μm.

According to some embodiments, low friction coating materials for the low friction coating(s) 60 are:

For Integrated Torque Jacket (ITJ): (Fiber Draw Coatings): DV acrylate fiber coatings with Fluroacrylates and/or Fluorosilanes additives.

a. For Integrated Torque Jacket (ITJ): (extruded Jackets): High Density Polyethylenes (HDP) with 3-5% of MR50-002 low friction commercial slip agent. An exemplary HDP is SAP Nr. 041545 Borstar HE6062, a Black Bimodal High Density Polyethylene Jacketing Compound for Energy and Communication Cables.

There are several advantages to utilizing coatings 60.

(1) The coatings can be applied on structural components like the annular structure 30 to minimize the frictional forces and provide better performance.

(2) Using low friction materials like Teflon and nylon or Polyimide can be expensive if all of the entire annular structure 30 is made of such materials. It would be less expensive to use thin coatings 60 on the outer surfaces of the annular structure 30.

Exemplary Teflon AF coating solution preparation: Teflon® AF (DuPont™ 1% in a fluoroether solvent, FC 40) is combined with a solution of adhesion binder (1 wt % in HFE7200) to produce a solution that is 1 wt % total in polymer mass. The solution is filtered through a coarse paper filter before use.

Exemplary coating and curing conditions: According to one embodiment, the metal tubular body (of the annular structure 30) with holes, slots, or other perforations therein is cleaned by wiping with ethanol soaked Kimwipe® and is dried thoroughly prior to use to remove organic contaminants on the surface. The coating is applied to the metal tubular body through immersion into the coating solution or other application method (contact transfer, spray coating, etc). The coated part is cured in an oven, ramping the temperature from 100° C. to 165° C. at 5 degrees/min, holding at 165° C. for 15 minutes, and then ramping the temperature to 280° C. at 5 degrees/minute, and then holding at 280° C. for 60 minutes.

Exemplary silane coating and curing conditions: 0.5% solution of heptadecafluorotetrahydrododecyltrichlorosilane (Gelest, Morrisville, Pa.) was prepared by combining the perfluorosilane with anhydrous heptane. The steel tubes (substrates) were cleaned by wiping with an ethanol soaked Kimwipe® and dried thoroughly prior to use. The substrate was immersed into the coating solution, allowed to sit for 1 minute and upon removal, rinsed with heptane followed by ethanol.

Adhesion binder preparation and details are described, for example in US published application, US20120189843.

Figure 7:
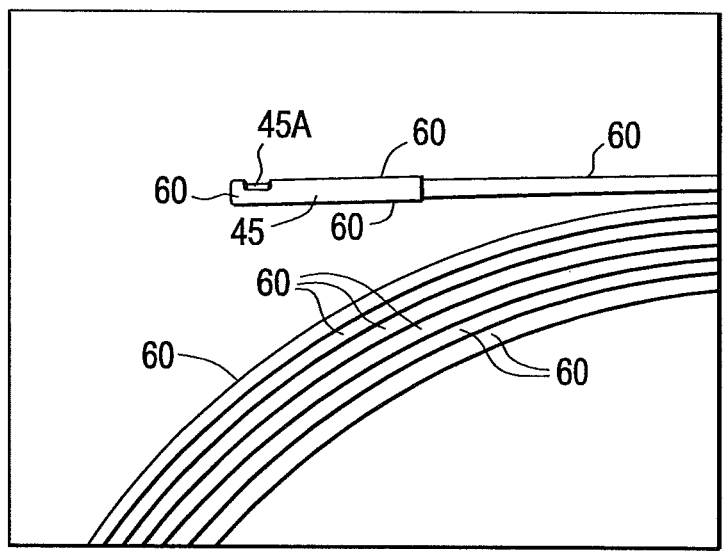
FIG. 7 illustrates one embodiment comprising a torque transmission component coated with a low friction coating, and metal OCT probe component attached thereto.

Tubular Housing. As mentioned above, one can use low frictional coatings 60 on the steel housing 45 (such as shown, for example, in FIG. 7) of the OCT probe components. The housing 45 is the leading edge of the OCT probe assembly and can be the source of a significant percentage of the frictional force in threading the OCT probe assembly into the inner lumen during the 3D scan. The coating 60 significantly reduces the frictional forces (e.g., by a factor of 2, or more) and significantly reduces the possibility of kinks, and inner lumen perforation. Such coatings 60 include, Teflon, low friction (typically fluoroalkyl silanes such as heptadecafluorotetrahydrodecyltrichlorosilane, as well as Dow Corning fluoroether silanes, DC2634, DC2604), silane surface treatments and other silicone coatings can be applied as a thin coating or surface treatment on the order of monolayers to hundreds of nanometers or thicker (micron range) if necessary.

Low friction coatings 60 on the surface(s) of the tubular housing 45 can be produced, for example, either by spray coating of low friction coating material(s) onto one or more surfaces of housing 45, or by a dip coating of low friction coating material(s), for example by dip coating the outer and/or inner surface of the housing 45. In some embodiments the outer surface 45' (surface closest to the inner lumen 48) of the tubular housing 45 is coated with low friction coating(s) 60. In some embodiments the inner (surface closest to the inner lumen) of the housing 45 is coated with low friction coating(s) 60, for example to minimize friction during insertion of the OCT optical prove component. In some embodiments all surfaces (including both the inner and the outer surfaces) of the housing 45 are coated with the low friction coating(s) 60. In some embodiments the thickness of low friction coating(s) 60 on the surfaces of the housing 45 is less than 100 μm, for example 0.1 μm to 10 μm. In some embodiments the low friction coating(s) 60 is situated on one or more surfaces of the tubular housing 45 and also on the outer surface of the annular structure 30. In some embodiments the low friction coating(s) 60 is situated on one or more surfaces of the tubular housing 45 and also on the outer surface of the annular structure 30. According to some embodiments, the low friction coating 60 for the tubular housing 45 is a Teflon or a nylon coating.

There are several advantages to utilizing coatings 60 on the tubular housing 45. The coating(s) 60 can be applied on structural components, for example the housing 45 of the OCT probe component in order to minimize the frictional forces between the tubular housing 45 and the inner lumen, and provide better performance. For packaging and mechanical structural reasons, it is preferable to use steel housing 45 to house the OCT optical probe component 10. To form a housing 45, according to some embodiments, commercially available medical tubes/needles are cut to size and then perforated to form a window 45A. The low friction coating(s) 60 are then applied on the outer surface and/or other surface(s) of the tubular body of the housing 45.

Exemplary coating and curing conditions for the tubular housing 45: The steel housing 45 is cleaned by wiping with ethanol soaked Kimwipe® and dried thoroughly prior to use to remove organic contaminants on the surface. Teflon® AF (DuPont™ 1% in a fluoroether solvent, FC 40) is combined with a solution of adhesion binder (1 wt % in HFE7200) to produce a solution that is 1 wt % total in polymer mass. The solution is filtered through a coarse paper filter before use. The coating is applied to the metal tubular body through immersion into the coating solution, or by other application method (contact transfer, spray coating, etc). The coated part is cured in an oven, for example, by ramping the temperature from 100° C. to 165 at 5 degrees/min, holding at 165° C. for 15 minutes, and then ramping the temperature to 280° C. at 5 degrees/minute, and then holding at 280° C. for 60 minutes.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. An OCT torque tube assembly comprising:
   (a) an OCT probe component;
   (b) an optical fiber connected to the OCT probe component;
   (c) a torque tube comprising an annular structure surrounding said optical fiber and structured to translating and rotating the OCT probe;
   wherein said annular structure of said torque tube is a tube that is: (i) does not have substantial elongation in axial direction; and (ii) has an inner wall and an outer wall, the inner wall being continuous; and
   wherein said annular structure of said torque tube (i) is structured to be bent to a bend radius r, where 2 cm <r<50 cm; and (ii) has elongation that is less than 5% when subjected to axial pull force.

2. The OCT torque tube assembly according to claim 1, wherein said annular structure of said torque tube is a tube that is not capable of substantial elongation in axial direction.

3. The OCT torque tube assembly of claim 1, wherein said annular structure of said torque tube comprises at least one of the following:
   (i) multilayers of polymers,
   (ii) multilayers of polymers with at least one of the polymer layers further including reinforcement elements;
   (iii) multilayers of polymers surrounding said fibers, said layers including at least one layer with rigidity <100 MPa and at least one layer with rigidity >400 MPa;
   (iv) a tubular body with multiple perforations around the circumferance and along the length of said tubular body.

4. The OCT torque tube assembly of claim 3 wherein at least one of the polymer layers includes silicone, thermal or uv curable crylate; and/or polyimide.

5. The OCT torque tube assembly of claim 1 wherein said annular structure comprises multilayers with at least one of polymer layer including mechanical reinforcement elements, said reinforcement elements include at least one of the following: wound interleaved metal wire; polymer mesh; carbon filaments, reinforcement fibers surrounding the optical fiber, or reinforcement fibers being embedded into the polymer.

6. The OCT torque tube assembly according to claim 1, wherein said annular structure comprises multilayers and said multilayers that are made of UV curable thermoplastic, or thermosetting materials.

7. The OCT torque tube assembly according to according to claim 1, wherein the outer most layer of said annular structure includes material with coefficient of friction being less than 0.3.

8. The OCT torque tube assembly according to claim 7, wherein the outer most layer of said annular structure includes at least one of the follows: Teflon, nylon, low friction filler beads with a diameter below 10 μm.

9. The OCT torque tube assembly according to claim 7, wherein the outer most layer of said annular structure comprises low friction filler beads with a diameter of less than 5 μm.

10. An OCT torque tube assembly according to claim 1 wherein said annular structure is an annular coating surrounding said fiber, wherein said coating and said fiber form a single monolithic component and said fiber in conjunction with said coating is structured to translate and rotate the OCT probe.

11. The OCT torque tube assembly according to claim 10, wherein said single monolithic component includes multi layers of polymers surrounding said fiber, said layers including at least one layer with rigidity <100 MPa and at least one layer with rigidity >400 MPa.

12. A power transmission assembly comprising:
   (a) an optical component;
   (b) an optical fiber, wherein said optical fiber is directly or indirectly attached to the optical component; and
   (c) a torque tube comprising an annular structure surrounding said fiber, said annular structure is structured to rotate and translate said optical component, wherein said annular structure of said torque tube has an outer most layer that includes a material with coefficient of friction being of less than 0.3;
   wherein said annular structure of said torque tube is a tube that is: (i) does not have substantial elongation in axial direction; and (ii) has an inner wall and an outer wall, the inner wall being continuous; and
   wherein said annular structure of said torque tube (i) is structured to be bent to a bend radius r, where 2 cm <r<50cm; and (ii) has elongation that is less than 5% when subjected to axial pull force.

13. A composite torque tube comprising:
   an optical fiber attached to a second component,
   and a torque tube surrounding said optical fiber, said torque tube comprising:
   (a) an annular structure said annular structure is structured to rotate and translate an optical component, said annular structure including multilayers of polymers, said multilayers layers including at least one layer with rigidity <100 MPa; and at least one layer with rigidity >400 MPa; and
   (b) an outer most layer including material with coefficient of friction being less than 0.3.

14. A torque tube assembly comprising the torque tube of claim 13, said torque tube assembly further including a tubular OCT probe housing coated with material with coefficient of friction being less than 0.3.

15. The torque tube assembly according to claim 14, wherein (a) said material includes at list one of the follows: Teflon, nylon, low friction filler beads with a diameter below 10 μm; and/or (ii) said material includes low friction filler beads with a diameter of less than 5 μm.

16. A torque tube of claim 13, wherein said annular structure is a tube not capable of substantial elongation in axial direction.

17. The OCT torque tube assembly according to claim 16, wherein said tube has an inner wall and an outer wall, the inner wall being continuous, said tube being flexible to be capable of being bent to a bend radius r, where 2 cm <r<50 cm.

* * * * *